(12) United States Patent
Salz et al.

(10) Patent No.: US 7,553,881 B2
(45) Date of Patent: Jun. 30, 2009

(54) DENTAL MATERIALS BASED ON RADICALLY POLYMERIZABLE MACROMERS WITH ANTIMICROBIAL EFFECT

(75) Inventors: Ulrich Salz, Lindau (DE); Jörg Zimmermann, Lustenau (AT); Dirk Poppe, Feldkirch (AT); Volker Rheinberger, Vaduz (LI); Jörg Tiller, Freiburg (DE); Christian Waschinski, Freiburg (DE)

(73) Assignee: Ivoclar Vivadent AG, Schaan (LI)

( * ) Notice: Subject to any disclaimer, the term of this patent is extended or adjusted under 35 U.S.C. 154(b) by 331 days.

(21) Appl. No.: 11/502,420

(22) Filed: Aug. 11, 2006

(65) Prior Publication Data

US 2007/0254979 A1    Nov. 1, 2007

(30) Foreign Application Priority Data

Apr. 28, 2006  (EP) .................................. 06113260

(51) Int. Cl.
*A61K 6/083*  (2006.01)
*C08F 26/06*  (2006.01)

(52) U.S. Cl. ........................ 523/116; 523/118; 523/122; 526/256; 526/265; 433/228.1

(58) Field of Classification Search ................. 523/116, 523/118, 122; 526/256, 265
See application file for complete search history.

(56) References Cited

U.S. PATENT DOCUMENTS

| | | | |
|---|---|---|---|
| 5,358,688 A | | 10/1994 | Robertson |
| 5,494,987 A | * | 2/1996 | Imazato et al. ............... 526/263 |
| 5,536,861 A | | 7/1996 | Robertson |
| 6,194,530 B1 | * | 2/2001 | Klesse et al. ................. 526/312 |
| 2003/0220416 A1 | | 11/2003 | Montgomery et al. |
| 2005/0080158 A1 | | 4/2005 | Ong et al. |

FOREIGN PATENT DOCUMENTS

| | | |
|---|---|---|
| DE | 195 46 965 C2 | 8/1999 |
| DE | 198 13 686 A1 | 9/1999 |
| EP | 0 537 774 B1 | 1/1998 |
| EP | 0 663 409 B1 | 10/1998 |
| EP | 0 705 590 B1 | 1/2002 |
| EP | 0 980 682 B1 | 2/2002 |
| WO | 98/48766 A1 | 11/1998 |
| WO | 00/69926 A1 | 11/2000 |
| WO | 01/90251 A1 | 11/2001 |
| WO | 2004/098658 A1 | 11/2004 |

OTHER PUBLICATIONS

A. H. Hogt et al., "Adhesion of coagulase-negative staphylococci to methacrylate polymers and copolymers", *Journal of Biomedical Materials Research*, vol. 20, pp. 533-545 (1986).
C. J. Waschinski et al., "Poly(oxazoline)s with Telechelic Antimicrobial Functions", *Biomacromolecules*, vol. 6, 2005, pp. 235-243.
C. J. Waschinski et al., "Influence of Satellite Groups on Telechelic Antimicrobial Functions of Polyoxazolines", *Macromol. Biosci.*, vol. 5, 2005, pp. 149-156.
A. D. Fuchs et al., "Antimicrobial Blockcopolymer Emulsifier for Contact-Active Polymer Suspensions and Surfaces", *Polymer Preprints*, vol. 45, No. 2, 2005, p. 1213.

* cited by examiner

*Primary Examiner*—Tae H Yoon
(74) *Attorney, Agent, or Firm*—Nixon Peabody LLP

(57) ABSTRACT

Dental material which contains at least one compound of the formula $[PG]_m—R^1—Z—SP—Y—R^2—[WG]_p$, in which m=1, 2 or 3; p=1, 2 or 3; $R^1$=is absent, a linear or branched $C_1$ to $C_{20}$ alkylene radical which can be interrupted one or more times by O, S, NH, SiR', CONH CONR', COO and/or OCONH, a substituted or unsubstituted, aromatic $C_6$ to $C_{14}$ radical or a combination thereof $R^2$=is absent, a linear or branched $C_1$ to $C_{20}$ alkylene radical which can be interrupted one or more times by O, S, NH, SiR', CONH CONR', COO and/or OCONH, a substituted or unsubstituted, aromatic $C_6$ to $C_{14}$ radical or a combination thereof; PG=a radically polymerizable group; SP=a polymeric spacer which is selected from polyethylene glycol, polypropylene glycol, polyglycerol, polyalkyloxazoline, polyethyleneimine, polyacrylic acid, polymethacrylic acid, polyvinyl alcohol, polyvinyl acetate, poly-(2-hydroxyethyl)acrylate, poly-(2-hydroxyethyl)methacrylate groups, hydrophilic polypeptide groups and copolymers of the corresponding monomers; WG=antimicrobially active group; Z=is absent, O, S, an ester, amide or urethane group; Y=is absent, O, S, an ester, amide or urethane group, and which has a molecular weight of at least 1,000.

25 Claims, No Drawings

DENTAL MATERIALS BASED ON RADICALLY POLYMERIZABLE MACROMERS WITH ANTIMICROBIAL EFFECT

This application claims priority, pursuant to 35 U.S.C. §119, to European Patent Application No. 06113260.1 filed Apr. 28, 2006, the entire content of which is incorporated by reference in its entirety.

FIELD

The present invention relates to dental materials based on antimicrobial, radically polymerizable macromers.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Polymers have long been given antimicrobial properties, usually by the purely physical mixing of an antimicrobial active ingredient into a corresponding material matrix. Thus for example in WO 98/48766 a tooth-coating material for the prevention of caries is described which contains triclosan (2,4,4'-trichloro-2'-hydroxydiphenylether) as antimicrobial active ingredient. Materials for dental use such as prosthetic plastics and fixing cements which contain antimicrobial phenolic substances such as triclosan are also described in US 2003/0220416.

DE 198 13 686 discloses a gutta-percha-based root-canal filling material which releases chlorhexidine as antimicrobial active ingredient.

US 2005/0080158 describes a UV-curing wood-coating material which contains triclosan, WO 2004/098658 proposes among other things the use of quaternary ammonium salts as antimicrobial active ingredients for polymeric coating materials for the building industry.

The purely physical mixing of antimicrobial active ingredients into a material is encumbered by several problems. In order to achieve its antimicrobial effect, the agent must be released over the period of action of the material. As a rule, the release rates are such that the agent is initially released in a very high concentration and thereafter the antimicrobial effect is largely lost. Another disadvantage is that at high agent concentrations toxic side-effects can occur, which is undesirable in particular in medical applications such as, e.g., contact lenses or dental materials. In addition, with continuous or increased release of agent there is a risk of resistance forming. For this reason, in particular for such applications, there has been a switch to making the agent polymerizable in order to immobilize it during the curing of the material by homopolymerization or copolymerization with another polymerizable monomer in the forming polymer.

U.S. Pat. No. 5,536,861 and U.S. Pat. No. 5,358,688 disclose organosilicone monomers which contain a quaternary ammonium group as antimicrobial group for use in contact lenses.

EP 0 663 409 discloses monomers which contain quaternary phosphonium groups as active group for use in contact lenses.

In EP 0 537 774 polymerizable active-ingredient monomers which contain a quaternary ammonium group are described. (Meth)acryl functionalities are used as polymerizable group, an alkylene spacer with 2 to 18 C atoms being located between the polymerizable group and the active group.

In EP 0 705 590 and WO 01/90251 special compositions for dental use which contain an antimicrobial, polymerizable monomer according to EP 0 537 774 are described.

A disadvantage when using polymerizable active ingredient monomers is that in most cases only the monomer has an antimicrobial effect, which is lost after the polymerization. Often, only residual monomer present is responsible for the antimicrobial effect of the polymers, with the result that after the elution of the non-polymerized antimicrobial monomers the antimicrobial effect of the materials diminishes. The antimicrobial long-term effect is thus significantly reduced, as a result of which, e.g., drugs or medicinal products at least partly lose their clinical capability.

DE 196 46 965 A1 discloses polymers with antimicrobial properties which consist of vinylically polymerizable monomers and of monomers in which at least one long-chained alkyl radical is bonded to a quaternary ammonium group which for its part is bonded via a hydrophilic spacer to a vinyl function. The polymers are to be suitable for the preparation of paints such as, e.g., marine paints and mouldings such as, e.g., bathroom and kitchen surfaces.

WO 00/69926 discloses a process for the preparation of inherently antimicrobial polymers by polymerization of monomers which have at least one quaternary amino function. The monomers can have a hydrocarbon radical with up to 50 carbon atoms and have a molecular mass of less than 900. The polymers are to be suitable for the preparation of varnishes, protective paints and coatings, e.g., for ship hulls, toiletries, contact lenses, membranes and implants.

SUMMARY

One aspect of the invention is to provide dental materials which in the polymerized state have a high antimicrobial effect and do not release an antimicrobially active component.

This can be achieved by dental materials which contain at least one antimicrobially active group.

According to one aspect, the present invention provides a dental material comprising at least one compound of Formula (I), $$[PG]_m—R^1—Z—SP—Y—R^2—[WG]_p \qquad (I)$$

in which m=1, 2 or 3; p=1, 2 or 3; $R^1$=is absent, a linear or branched $C_1$ to $C_{20}$ alkylene radical which can be interrupted one or more times by O, S, NH, SiR'$_2$, CONH, CONR', COO and/or OCONH, a substituted or unsubstituted, aromatic $C_6$ to $C_{14}$ radical or a combination thereof, $R^2$=is absent, a linear or branched $C_1$ to $C_{20}$ alkylene radical which can be interrupted one or more times by O, S, NH, SiR'2, CONH, CONR', COO and/or OCONH, a substituted or unsubstituted, aromatic $C_6$ to $C_{14}$ radical or a combination thereof, PG=a radically polymerizable group, SP=a polymeric spacer which is selected from polyethylene glycol, polypropylene glycol, polyglycerol, polyalkyloxazoline, polyethyleneimine, polyacrylic acid, polymethacrylic acid, polyvinyl alcohol, polyvinyl acetate, poly-(2-hydroxyethyl)acrylate, poly-(2-hydroxyethyl)methacrylate groups, hydrophilic polypeptide groups and copolymers of the corresponding monomers, WG=an antimicrobially active group, Z=is absent, O, S, an ester, amide or urethane group, Y=is absent, O, S, an ester, amide or urethane group, and which has a molecular weight of at least 1,000.

DETAILED DESCRIPTION

According to certain embodiments, there are provided dental materials comprising at least one compound composed according to Formula (I):

$$[PG]_m—R^1—Z—SP—Y—R^2—[WG]_p \quad (I)$$

in which the variables have the following meanings:

m=1, 2 or 3;
p=1, 2 or 3;
$R^1$=is absent, a linear or branched $C_1$ to $C_{20}$ alkylene radical which can be interrupted one or more times by O, S, NH, SiR'$_2$, CONH, CONR', COO and/or OCONH, a substituted or unsubstituted, aromatic $C_6$ to $C_{14}$ radical or a combination thereof;
$R^2$=is absent, a linear or branched $C_1$ to $C_{20}$ alkylene radical which can be interrupted one or more times by O, S, NH, SiR'$_2$, CONH, CONR', COO and/or OCONH, a substituted or unsubstituted, aromatic $C_6$ to $C_{14}$ radical or a combination thereof;
PG=a radically polymerizable group;
SP=a polymeric spacer which is preferably selected from polyethylene glycol, polypropylene glycol, in particular polyglycerol, polyalkyloxazoline, polyethyleneimine, polyacrylic acid, polymethacrylic acid, polyvinyl alcohol, polyvinyl acetate, poly-(2-hydroxyethyl)acrylate-, poly-(2-hydroxyethyl)methacrylate groups, hydrophilic polypeptide groups and copolymers, in particular block copolymers of the corresponding monomers;
WG=an antimicrobially active group;
Z=is absent, O, S, an ester, amide or urethane group;
Y=is absent, O, S, an ester, amide or urethane group.

R' represents independently in each case a linear or branched $C_1$ to $C_{20}$ alkylene radical, a substituted or unsubstituted phenyl or benzyl radical.

The substituents optionally present in the case of $R^1$, $R^2$, and R' are selected independently of each other, preferably from $C_1$-$C_6$ alkyl, $C_1$-$C_6$ alkoxyl, aryl, benzyl, F, Cl, Br, I, HO, HOOC, $C_1$-$C_6$ alkyl-OOC—, $H_2$NOC, HR"OC and R"$_2$OC, wherein R" is a $C_1$-$C_{20}$ alkylene, phenyl or benzyl radical.

Formula (I) covers only those compounds which are compatible with the theory of chemical valence. The indication that a radical can be interrupted, e.g., by O, S, NH, SiR', CONH, CONR', COO, OCONH etc., is to be understood to mean that these atoms or groups are inserted into the carbon chain of the radical, i.e., are bordered on both sides by carbon atoms. The number of these foreign atoms or groups is therefore at least 1 less than the number of carbon atoms, and the foreign atoms or groups cannot be terminal.

By combinations of alkylene radicals and aromatic groups are preferably meant alkylene-arylene, alkylene-arylene-alkylene and arylenealkylene-arylene groups, in particular —CH$_2$—Ph and —CH$_2$—Ph—CH$_2$— groups.

The compound of Formula (I) has a molecular weight of at least 1,000 g/mol, preferably at least 2,500 g/mol and particularly preferably at least 5,000 g/mol. The compound of Formula (I) contains at least one radically polymerizable group and can thus be cured by radical polymerization. It is also called a macromer in the following.

Preferred polymerizable groups (PG) are vinyl CH$_2$=CH—, allyl CH$_2$=CH—CH$_2$—, vinyl ether CH$_2$=CH—O—, styryl CH$_2$=CH—(Ph)—, vinylcyclopropyl groups and/or groups of Formula (II),

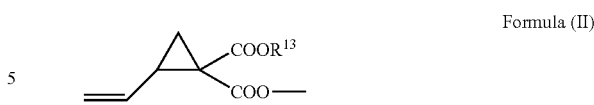

Formula (II)

in which $R^{13}$ is methyl or phenyl.

Quite particularly preferred polymerizable groups PG are (meth)acryloyl CH$_2$=C(CH$_3$)—COO— and (meth)acrylamide groups CH$_2$=C(CH$_3$)—CO—NH—.

The antimicrobial group (WG) can be a primary, secondary, or tertiary amino group, a cationic primary, secondary, tertiary or quaternary ammonium, phosphonium or sulphonium group, a biguanidine group, an antimicrobial peptide, a phenol or polyphenol radical and/or an antibiotic. Preferred antimicrobial groups are quaternary ammonium groups, phosphonium groups and sulphonium groups.

By primary, secondary, tertiary and quaternary ammonium groups are meant groups of formula (—N$^+$RH$_3$), (—N$^+$R$_2$H$_2$), (—N$^+$R$_3$H) and (—N$^+$R$_4$).

Preferred antibiotics are penicillin groups, in particular:

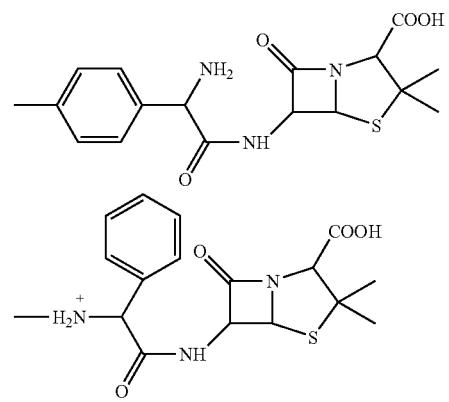

The antimicrobial group WG can have a positive charge. This is

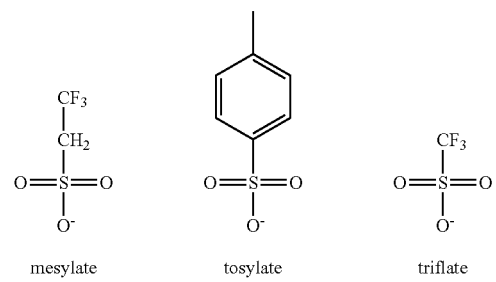

mesylate   tosylate   triflate balanced by A$^-$ anions. Preferred A$^-$ anions are Cl$^-$, Br$^-$, I$^-$, triflate (Trf), mesylate (Mes) and tosylate (Tos):

According to a preferred embodiment, the spacer SP is a group with the formula —[R$^3$]$_q$— in which R$^3$ is —[CH$_2$—CH$_2$—O]—, —[CH(CH$_3$)—CH$_2$—O]—, preferably —[CH(OH)CH$_2$]—, —[CH(COOH)CH$_2$]—, —[CH(COOCH$_3$)CH$_2$]—, —[C(CH$_3$)(COOH)CH$_2$]—, —[C(CH$_3$)(COOCH$_3$)CH$_2$]—, —[CH(COOCH$_2$CH$_2$OH)CH$_2$]—, —[C(CH$_3$)(COOCH$_2$CH$_2$OH)CH$_2$]—, —[CH(OCOCH$_3$)CH$_2$]—, —[CH$_2$—CH(OH)—CH$_2$—O]— and in particular —[R$^4$—N(—CO—R$^6$)—R$^5$]— or a combination thereof, wherein R$^4$=is absent, a linear or branched C$_1$ to C$_{20}$ alkylene radical which can be interrupted by one or more O atoms, a substituted or unsubstituted, aromatic C$_6$ to C$_{14}$ radical, preferably —(CH$_2$)$_{1-4}$— and in particular is absent;

R$^5$=is absent, a linear or branched C$_1$ to C$_{20}$ alkylene radical which can be interrupted by one or more O atoms, a substituted or unsubstituted, aromatic C$_6$ to C$_{14}$ radical, preferably —(CH$_2$)$_{1-4}$— or is absent, in particular —(CH$_2$)$_2$—;

R$^6$=a linear or branched C$_1$ to C$_{20}$ alkyl radical, a substituted or unsubstituted, aromatic C$_6$ to C$_{14}$ radical, preferably C$_1$-C$_3$ alkyl, in particular methyl;

q=10 to 15,000, preferably 10 to 10,000, particularly preferably 10 to 5,000, quite particularly preferably 15 to 2,000.

R$^4$ and R$^5$ are preferably not absent at the same time. A quite particularly preferred group of formula —[R$^3$]— is —[N(COCH$_3$)—CH$_2$—CH$_2$]—.

The substituents optionally present in the case of R$^4$, R$^5$, and R$^6$ are selected independently of each other preferably from C$_1$-C$_6$ alkyl, C$_1$-C$_6$ alkoxyl, aryl, benzyl, F, Cl, Br, I, HO, HOOC, C$_1$-C$_6$ alkyl-OOC—, H$_2$NOC—, HR"OC— and R"$_2$OC—, wherein R" is a C$_1$-C$_{20}$ alkylene, phenyl or benzyl radical.

Compounds in which the spacer is a group of formula —[R$^3$]$_q$— can be represented by the general Formula (I'):

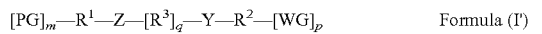

[PG]$_m$—R$^1$—Z—[R$^3$]$_q$—Y—R$^2$—[WG]$_p$       Formula (I')

in which the other variables have the meanings given above.

Preferred definitions of the other variables which can be chosen independently of one another are:

m=1 or 2, in particular 1;
p=1 or 2, in particular 1;
R$^1$=is absent, a linear or branched C$_1$ to C$_4$ alkylene radical which can be interrupted once by COO, phenylene, benzylene, —CH$_2$—Ph—CH$_2$—;
R$^2$=is absent, a linear or branched C$_1$ to C$_4$ alkylene radical which can be interrupted once by COO, phenylene, benzylene, —CH$_2$—Ph—CH$_2$—;
PG=CH$_2$=CR$^{10}$—CO—X— with R$^{10}$=H or CH$_3$ and X=O, NH, NR$^{12}$, wherein R$^{12}$ is a linear C$_1$ to C$_5$ alkyl radical, preferably methyl, CH$_2$=CH— or vinylcyclopropyl;
Z=is absent, O, S, COO, preferably absent, O, S;
Y=is absent, O, S, COO; preferably absent;
A$^-$=Cl$^-$, Br$^-$, I$^-$, mesylate (Mes), tosylate (Tos) or triflate (Trf);
WG=—N$^+$R$^7$R$^8$R$^9$A$^-$, with
R$^7$=H, a linear or branched C$_1$ to C$_{20}$ alkyl radical, or R$^7$ forms together with R$^8$ and the nitrogen atom to which it is bonded an aromatic or heteroaromatic ring system or an aromatic or non-aromatic ring, preferably a C$_1$ to C$_6$ alkyl radical, particularly preferably CH$_3$;

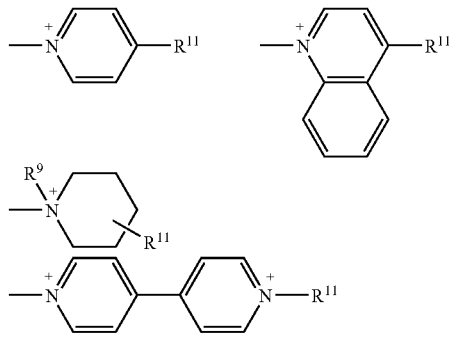

wherein R$^{11}$ is a linear or branched C$_1$ to C$_{20}$ alkyl radical;
R$^8$=H, a linear or branched C$_1$ to C$_{20}$ alkyl radical or R$^8$ forms together with R$^7$ and the nitrogen atom to which it is bonded an aromatic or heteroaromatic ring system or an aromatic or non-aromatic ring, preferably a C$_1$ to C$_6$ alkyl radical, particularly preferably CH$_3$;
R$^9$=is absent, H, a linear or branched C$_1$ to C$_{31}$ alkyl radical, preferably —(CH$_2$)$_r$—;
r=5 to 30, preferably 10 to 30, particularly preferably 10 to 20;
—P$^+$R$^{7'}$R$^{8'}$R$^{9'}$A$^-$, with
R$^{7'}$=H, a linear or branched C$_1$ to C$_{20}$ alkyl radical, preferably a C$_1$ to C$_6$ alkyl radical, particularly preferably CH$_3$;
R$^{8'}$=H, a linear or branched C$_1$ to C$_{20}$ alkyl radical, preferably methyl;
R$^{9'}$=is absent, H, a linear or branched C$_1$ to C$_{20}$ alkyl radical, preferably —(CH$_2$)$_r$—;
r=5 to 30, preferably 10 to 30, particularly preferably 10 to 20;
or

r=5 to 30, preferably 10 to 30, particularly preferably 10 to 20.

Particularly preferred are naturally compounds in which all the variables have one of the preferred and in particular of the particularly preferred meanings.

Particularly preferred compounds of formula (I') are:

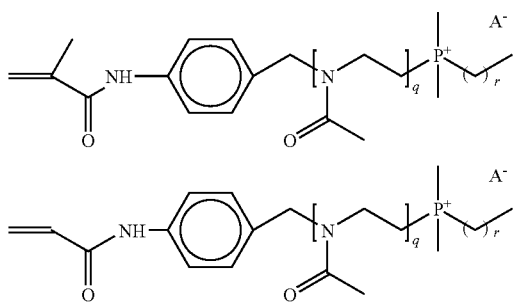

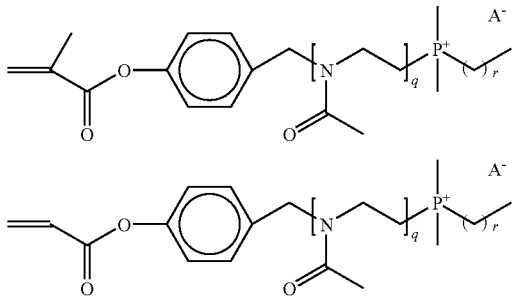

-continued
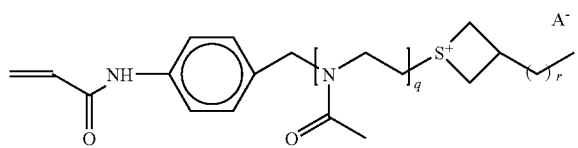
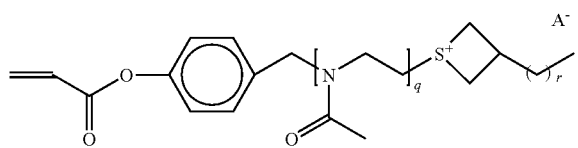
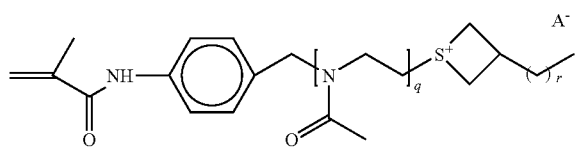
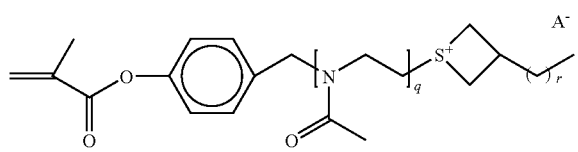
A⁻ = Cl⁻, Br⁻, I⁻, Trf, Mes, Tos
q = 10 to 10,000
r = 10 to 20
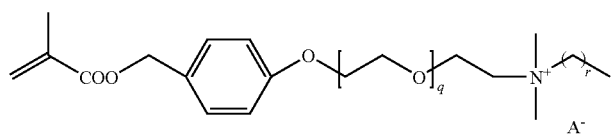
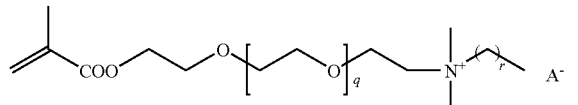
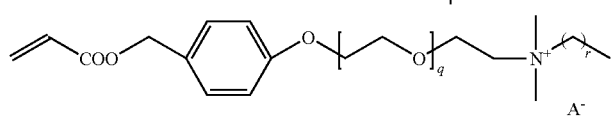
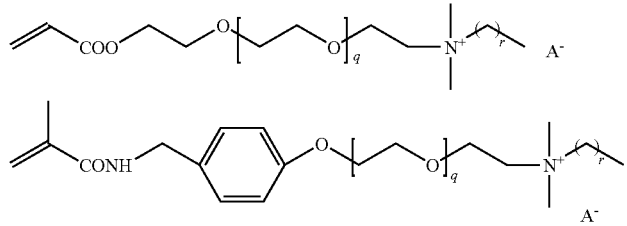
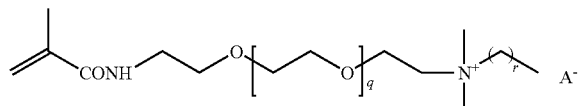
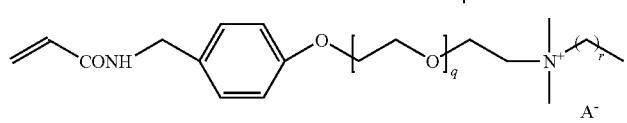
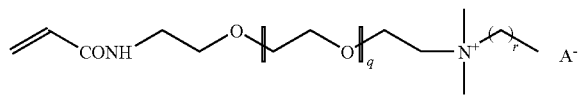
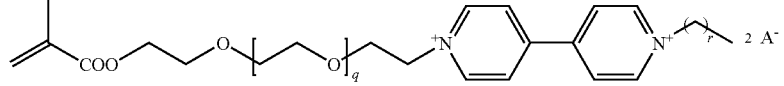

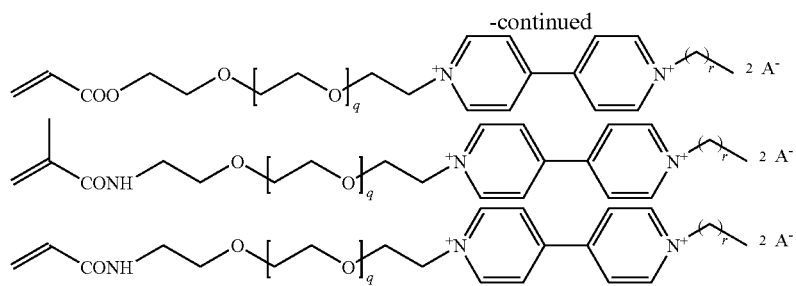
-continued
A⁻ = Cl⁻, Br⁻, I⁻, Trf, Mes, Tos
q = 45 to 15,000
r = 10 to 20
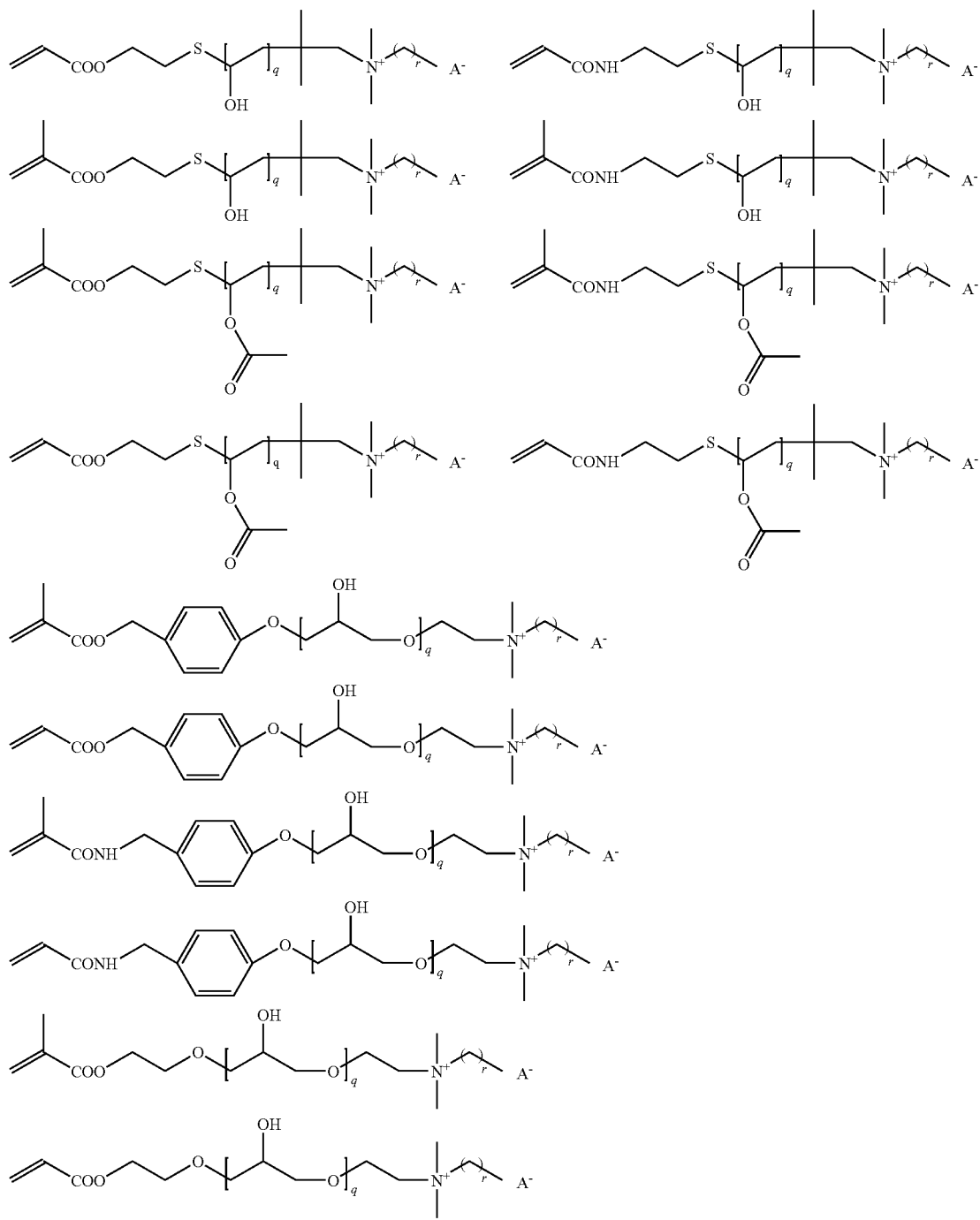

-continued
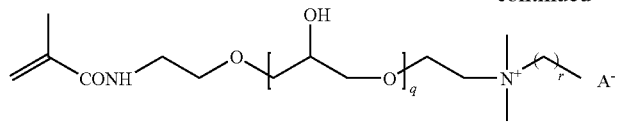
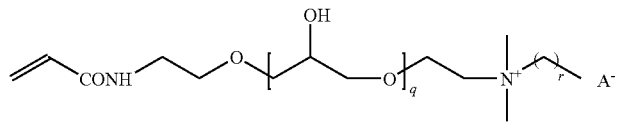
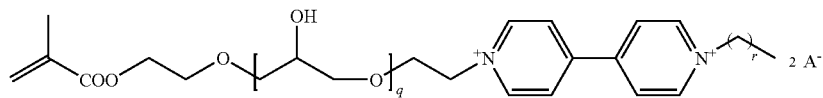
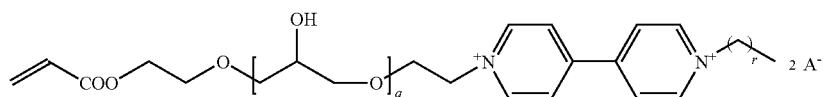
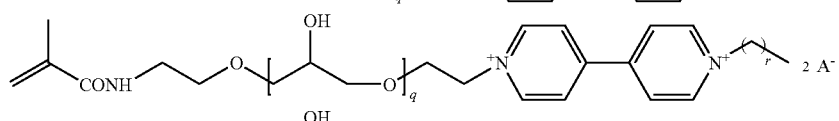
A⁻ = Cl⁻, Br⁻, I⁻, Trf, Mes, Tos
q = 10 to 10,000
r = 10 to 20
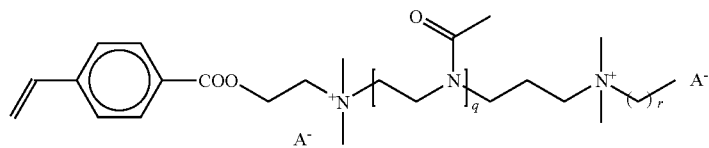
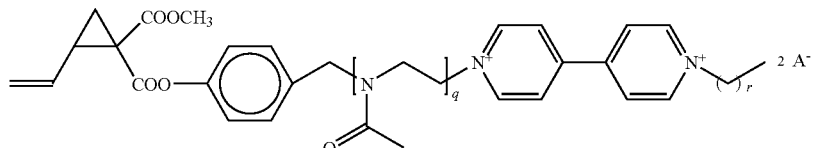
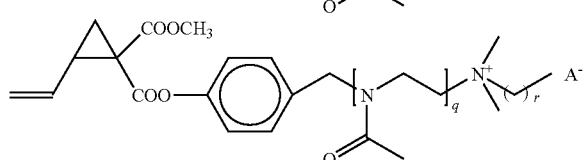
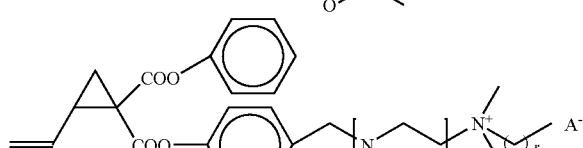
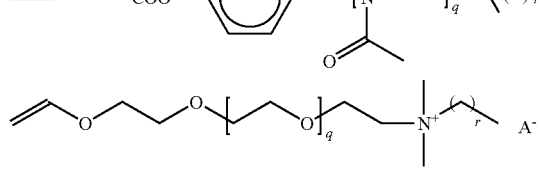
A⁻ = Cl⁻, Br⁻, I⁻, Trf, Mes, Tos
q = 10 to 10,000
r = 10 to 20

Compounds of Formula (I″)
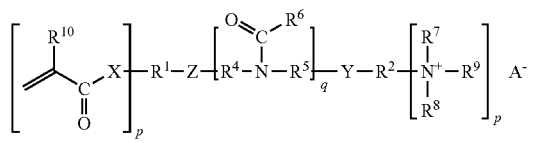
Formula (I″)
in which the variables have the above-mentioned meanings and preferred meanings are quite particularly preferred.
Preferred examples of the macromers of Formula (I″) with a polyoxazoline spacer are:
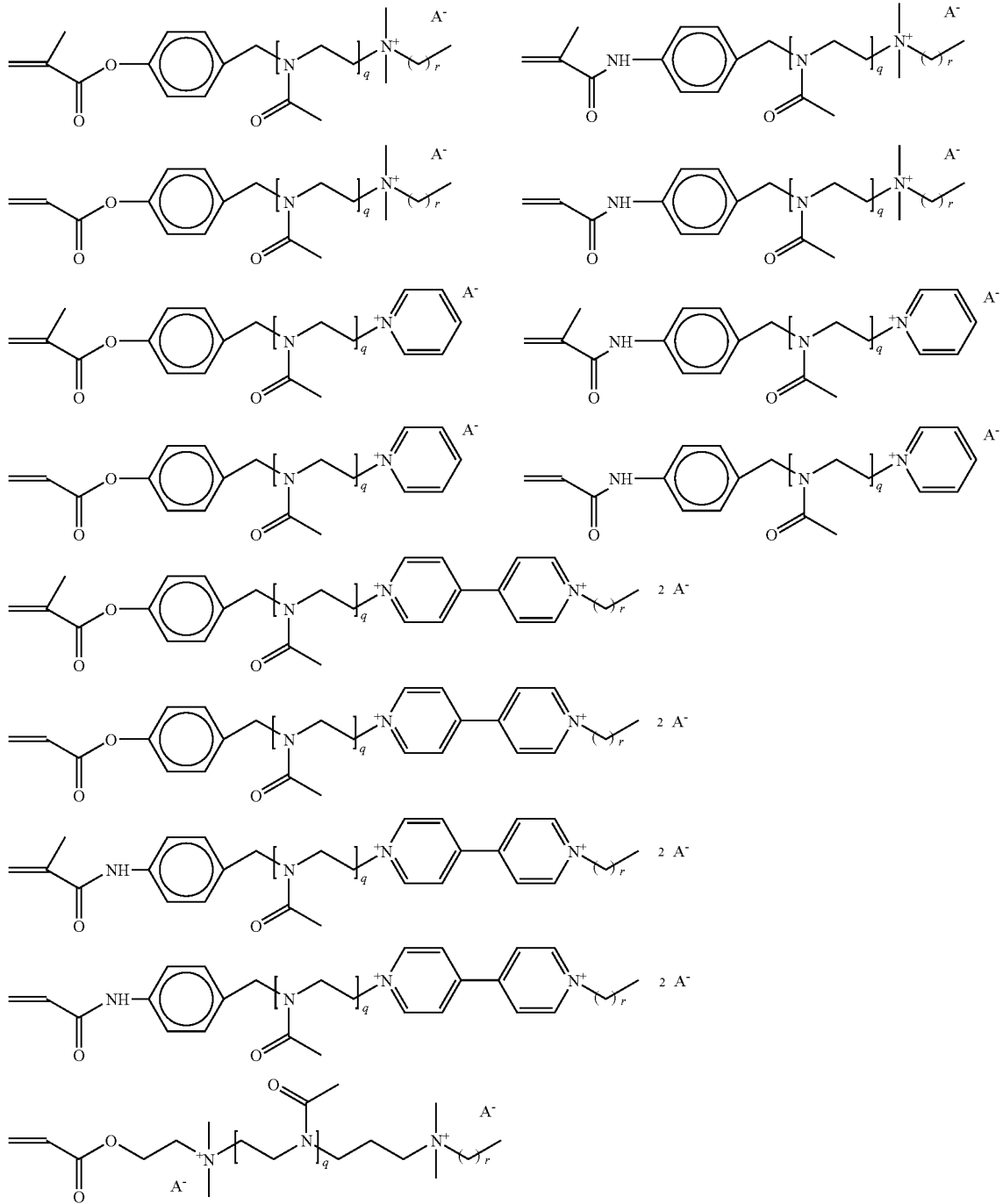

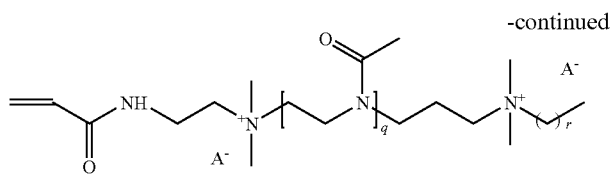

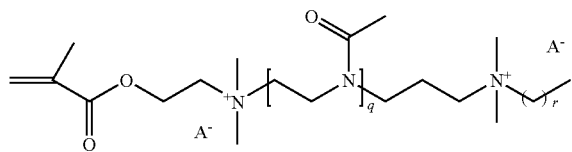

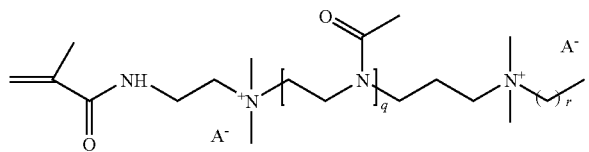

A⁻ = Cl⁻, Br⁻, I⁻, Trf, Mes, Tos
q = 10 to 10,000
r = 10 to 20

The antimicrobial, polymerizable macromers of general Formula (I) can be prepared by known multi-stage synthesis methods. For example the particularly preferred antimicrobial, polymerizable macromers of Formula (I″) with a polyoxazoline spacer can be prepared in the following ways.

In a first synthesis variant, in the first stage the polymer spacer (SP) is built up by polymerization of 2-alkyl-1,3-oxazoline. The degree of polymerization and thus the spacer length is controlled via the monomer-initiator ratio $[M_0]/[I]$ and the reaction time. A tertiary amine is used to terminate the polymerization, wherein the corresponding antimicrobially active quaternary ammonium group (WG) forms therefrom. After removal of the protective group, the polymerizable group (PG) is introduced by reaction of the deprotected amine with methacrylic acid or acrylic acid chloride. The corresponding methacryl- or acrylamide forms.

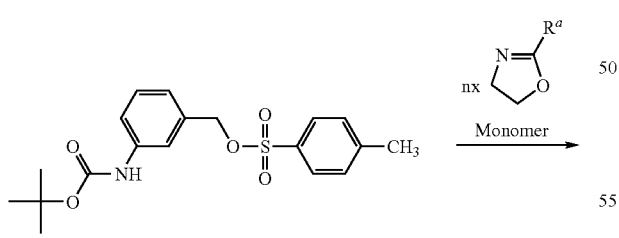

Initiator

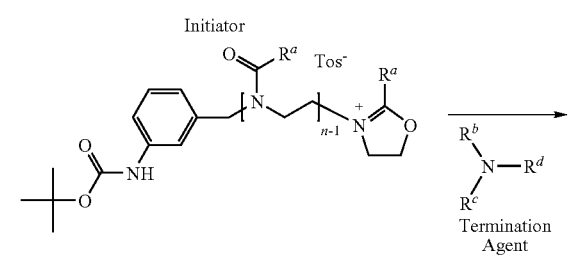

Termination Agent

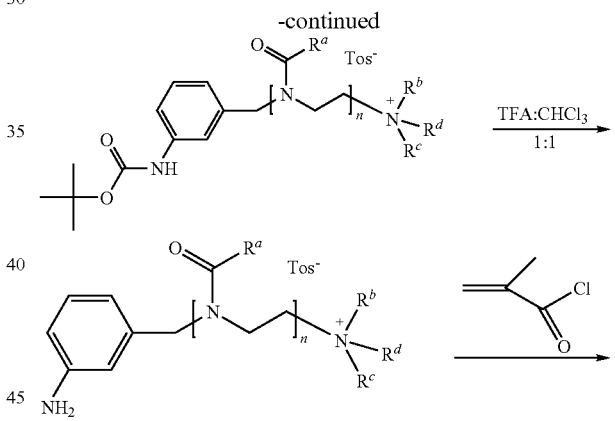

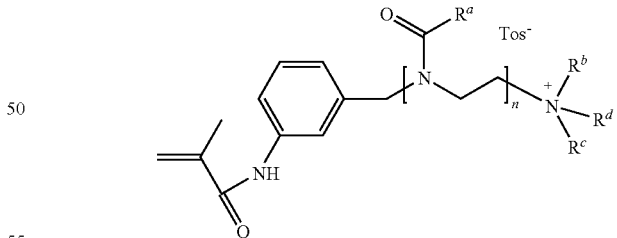

In a second synthesis variant, the polymeric spacer is likewise built up by polymerization of 2-alkyl-1,3-oxazolines. In this case also, as with the first synthesis variant, the degree of polymerization and thus the spacer length are controlled via the monomer-initiator ratio and the reaction time. The antimicrobially active quaternary ammonium group (WG) is introduced by the initiator, the polymerizable group (PG) at the other end of the polymer being obtained by terminating the reaction with amines which contain polymerizable groups.

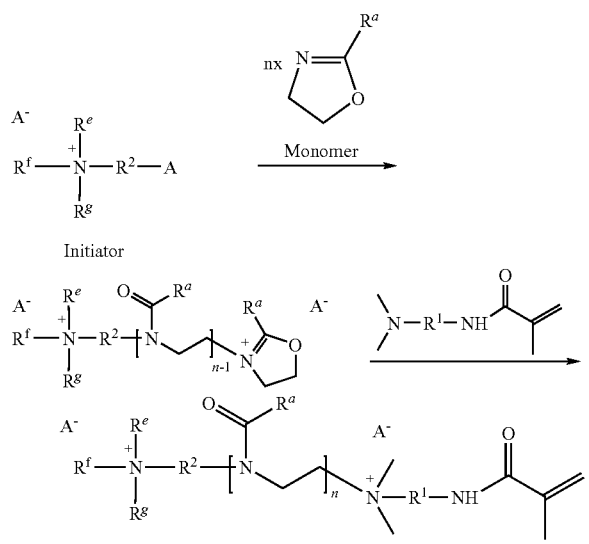

The macromers of Formula (I) can be converted by homopolymerization or by copolymerization with further macromers of Formula (I) and/or other radically polymerizable monomers into polymers in which the antimicrobial component is immobilized and is not washed out.

The dental materials can contain, in addition to the macromers of Formula (I), further radically polymerizable monomers with one or more radically polymerizable groups. Dental materials which contain at least one further radically polymerizable monomer with 2 or more, preferably 2 to 3, radically polymerizable groups, are particularly preferred.

Preferred additional monomers are mono- or polyfunctional (meth)acrylates or (meth)acrylamides ((meth)acrylic compounds). By monofunctional (meth)acrylic compounds are meant compounds with one, by polyfunctional (meth)acrylic compounds, compounds with two or more, preferably 2 to 3, (meth)acrylic groups. Polyfunctional monomers have cross-linking properties.

Preferred monofunctional (meth)acrylic compounds are commercially available monofunctional monomers, such as methyl, ethyl, butyl, benzyl, furfuryl or phenyl(meth)acrylate as well as 2-hydroxyethyl or propyl(meth)acrylate.

Particularly preferred are hydrolysis-stable monomers such as hydrolysis-stable mono(meth)acrylates, e.g., mesityl methacrylate or 2-(alkoxymethyl)acrylic acids, e.g., 2-(ethoxymethyl)acrylic acid, 2-(hydroxymethyl)acrylic acid, N-mono- or -disubstituted acrylamides, such as, e.g., N-ethylacrylamide, N,N-dimethacrylamide, N-(2-hydroxyethyl)acrylamide or N-methyl-N-(2-hydroxyethyl)acrylamide, and N-monosubstituted methacrylamides, such as, e.g., N-ethylmethacrylamide or N-(2-hydroxyethyl)methacrylamide as well as N-vinylpyrrolidone and allyl ethers. These monomers are liquid at room temperature and are therefore suitable as diluents.

Preferred polyfunctional monomers are bisphenol-A-di(meth)acrylate, bis-GMA (an addition product of methacrylic acid and bisphenol-A-diglycidyl ether), ethoxylated bisphenol-A-di(meth)acrylate, UDMA (an addition product of 2-hydroxyethyl methacrylate and 2,2,4-trimethylhexamethylene diisocyanate), di-, tri- or tetraethyleneglycol di(meth)acrylate, trimethylolpropane tri(meth)acrylate, pentaerythritol tetra(meth)acrylate, as well as butanediol di(meth)acrylate, 1,10-decanediol di(meth)acrylate or 1,12-dodecanediol di(meth)acrylate.

Particularly preferred are furthermore hydrolysis-stable cross-linking monomers, such as, e.g., cross-linking pyrrolidones, such as, e.g., 1,6-bis(3-vinyl-2-pyrrolidonyl)-hexane, or commercially available bisacrylamides such as methylene or ethylenebisacrylamide, bis-(meth)acrylamides, such as, e.g., N,N'-diethyl-1,3-bis-(acrylamido)-propane, 1,3-bis-(methacrylamido)propane, 1,4-bis-(acrylamido)-butane or 1,4-bis-(acryloyl)-piperazine which can be synthesized by conversion from the corresponding diamines with (meth)acrylic acid chloride.

The dental materials preferably also contain at least one radically polymerizable, acid-group-containing monomer. Acid-group-containing monomers are also called acidic monomers in the following. Preferred acid groups are carboxylic acid groups, phosphonic acid groups, phosphate groups and/or sulphonic acid groups, wherein these groups can be present in acid form or in the form of an ester. Monomers with phosphonic acid groups or phosphate groups are particularly preferred. The monomers can have one or more acid groups, compounds with 1 to 2 acid groups being preferred.

Preferred polymerizable carboxylic acids are maleic acid, acrylic acid, methacrylic acid, 2-(hydroxymethyl)acrylic acid, 4-(meth)acryloyloxyethyltrimellitic acid and the corresponding anhydride, 10-methacryloyloxydecylmalonic acid, N-(2-hydroxy-3-methacryloyloxypropyl)-N-phenylglycine and 4-vinylbenzoic acid.

Preferred phosphonic acidic monomers are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid and 2-[2-dihydroxyphosphoryl)-ethoxymethyl]-acrylic acid-2,4,6-trimethyl-phenyl ester.

Preferred acidic polymerizable phosphoric acid esters are 2-methacryloyloxypropylmono- and -dihydrogen phosphate, 2-methacryloyloxyethylmono- and -dihydrogen phosphate, 2-methacryloyloxyethyl-phenyl-hydrogen phosphate, dipentaerythritolpentamethacryloyloxyphosphate, 10-methacryloyloxydecyl-dihydrogen phosphate, dipentaerythritolpentamethacryloyloxyphosphate, phosphoric acid mono-(1-acryloyl-piperidine-4-yl)-ester, 6-(methacrylamido) hexyldihydrogen phosphate and 1,3-bis-(N-acryloyl-N-propyl-amino)-propan-2-yl-dihydrogen phosphate.

Preferred polymerizable sulphonic acids are vinyl sulphonic acid, 4-vinylphenyl sulphonic acid or 3-(methacrylamido)propyl sulphonic acid.

Acylphosphine oxides, bisacylphosphine oxides, benzophenone, benzoin as well as their derivatives or α-diketones or their derivatives such as 9,10-phenanthrenequinone, 1-phenyl-propan-1,2-dione, diacetyl or 4,4-dichlorobenzil are preferably used to initiate the radical photopolymerization. Camphorquinone and 2,2-methoxy-2-phenyl-acetophenone are preferably, and α-diketones combined with amines particularly preferably, used as reducing agents, such as, e.g., 4-(dimethylamino)-benzoic acid ester, N,N-dimethylaminoethylmethacrylate, N,N-dimethyl-sym.-xylidine or triethanolamine. Combinations of different photoinitiators are also used.

Redox-initiator combinations, such as, e.g., combinations of benzoyl peroxide with N,N-dimethylsym.-xylidine or N,N-dimethyl-p-toluidine, are used as initiators for a so-called chemical curing. In addition, redox systems consisting of peroxides and reducing agents, such as, e.g., ascorbic acid, barbiturates or sulphinic acids, are particularly suitable.

Furthermore the dental materials can contain organic or inorganic particulate fillers to improve the mechanical properties or to set the viscosity. Preferred inorganic particulate fillers are amorphous spherical materials based on oxides, such as $ZrO_2$ and $TiO_2$, nanoparticulate or microfine fillers such as pyrogenic silica, nanoparticulate $Al_2O_3$, $Ta_2O_5$, $Yb_2O_3$, $ZrO_2$, Ag or $TiO_2$ or mixed oxides of $SiO_2$, $ZrO_2$ and/or $TiO_2$ or precipitated silica acid as well as minifillers, such as quartz, glass ceramic or glass powder with an average particle size of 0.01 to 1 μm as well as X-ray-opaque fillers, such as ytterbium trifluoride or nanoparticulate barium sulphate. Fillers which are surface-modified with polymerizable groups are particularly suitable.

Moreover, the dental materials can contain one or more further additives which are preferably selected from stabilizers, inhibitors, aromatics, dyes, pigments, fluoride-ion-releasing additives, optical brighteners, plasticizers and/or UV absorbers. A preferred UV absorber is 2-hydroxy-4-methoxybenzophenone, preferred stabilizers are 2,6-di-tert-butyl-4-cresol and 4-methoxyphenol.

The dental materials are in particular suitable as filling materials and especially as coating materials, adhesives, self-adhesive and/or self-conditioning fixing cements.

The dental materials preferably contain:
(a) 0.05 to 50.0 wt.-%, preferably 0.5 to 25.0 wt.-% and particularly preferably 2.0 to 10.0 wt.-% antimicrobial, radically polymerizable macromer of Formula (I);
(b) 5 to 95 wt.-%, preferably 5 to 85 wt.-% and particularly preferably 5 to 70 wt.-% further radically polymerizable monomer;
(c) 0.01-5.0 wt.-% initiator for the radical polymerization.

Moreover, the dental materials according to the invention preferably also contain:

(d) 0 to 60 wt.-%, preferably 5 to 50 wt.-% and particularly preferably 5 to 45 wt.-% acidic radically polymerizable monomer and/or
(e) 0 to 85 wt.-% filler and/or
(f) 0 to 80 wt.-%, preferably 0 to 60 wt.-% and particularly preferably 0 to 40 wt.-% solvent and/or
(g) 0.01 to 5.0 wt.-%, preferably 0.01 to 3.0 wt.-% further additives.

Solvents are mainly used in adhesives and coating materials. Preferred solvents are water, methanol, ethanol, isopropanol, ethyl acetate, acetone and mixtures thereof.

The precise filler content of the dental materials is based on the intended use of the materials. Dental materials for use as adhesive or coating material preferably contain 0 to 30 wt.-% and dental materials for use as cement or filling material preferably 20 to 85 wt.-% filler.

The antimicrobial, radically polymerizable macromers of Formula (I) can be used for the preparation of dental materials, preferably the dental materials described above.

In addition, processes are contemplated for the preparation of mouldings, such as crowns, bridges, inlays and artificial teeth, in which a dental material according to the invention is shaped to form the molding in a manner known per se and then at least partly, preferably fully, cured. The curing preferably takes place by radical polymerization.

The above principles are described in further detail by reference to the following illustrative, non-limiting examples.

EXAMPLES

Example 1

Preparation of Macromers with Polyoxazoline Spacer Beginning with Initiator

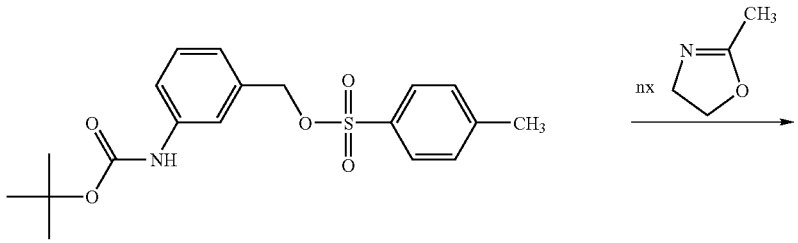

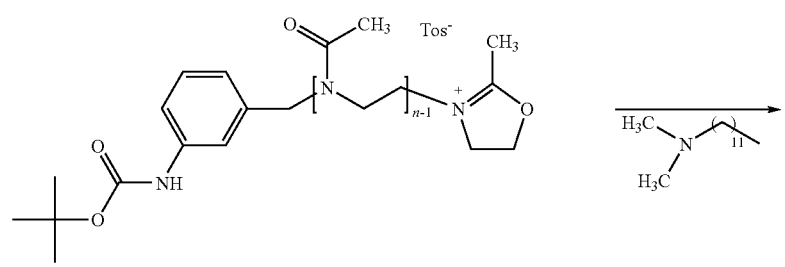

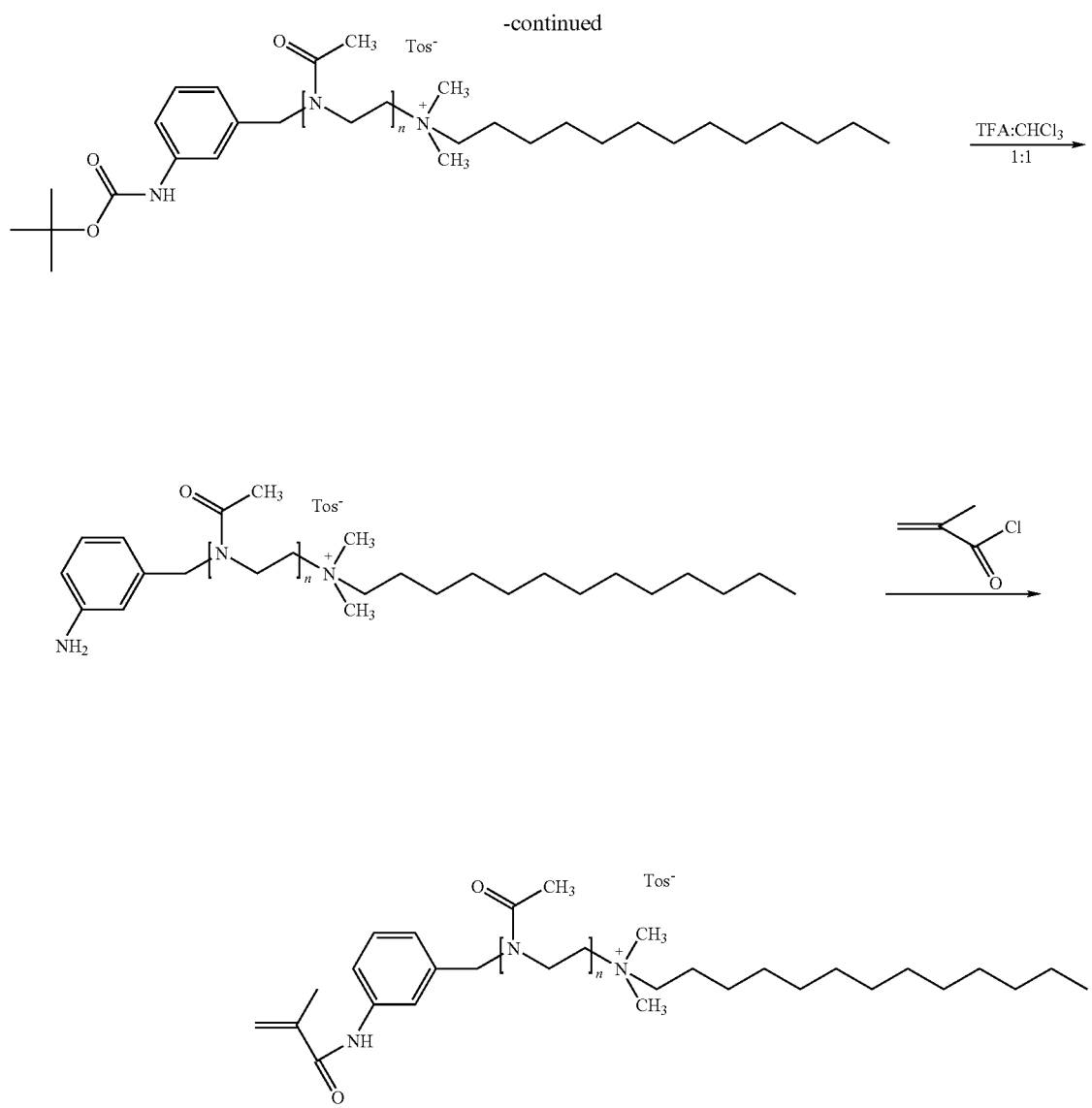

0.2 g of the initiator 3-[(tert-butoxycarbonyl)amino]benzyl-p-toluenesulphonate was added to a solution of 2-methyl-1,3-oxazoline (5.0 g) in 25 ml CHCl₃ at 0° C. After 30 min, the mixture was heated to 70° C., and the batch was stirred for three days. 4.0 g (5.0 ml; 18.0 mmol) of the termination reagent N,N-dimethyldodecylamine was then added and the whole stirred for a further 24 h at 70° C. After precipitation three times from diethyl ether and dialysis in water at RT, the light-yellow, powdery polymer was obtained.

Splitting off the protective group: approx. 3 g polymer was dissolved in a 1:1 mixture of trifluoroacetic acid and dichloromethane (6+6 ml) and stirred for 30 min at room temperature, wherein a strong gas formation was to be observed. The polymer deprotected in this way was then worked up as in the actual polymer synthesis (recrystallization from diethyl ether).

Reaction of the free amino function with methacrylic acid chloride: 1.1 g methacrylic acid chloride was added dropwise at 0° C. to a solution of 2.8 g of the deprotected polymer and 1.2 g pyridine in 15 ml chloroform. After 2 h, the mixture was brought to RT and the solution was stirred for a further 24 h. After precipitation three times from diethyl ether and dialysis in water at RT, 2.4 g (83% of the theoretical value) of the light-yellow, powdery macromer 1a was obtained.

The macromers 1b and 1c were prepared in the same way as macromer 1a, the difference being that for preparation of macromer 1b a monomer/initiator ratio (2-methyl-1,3-oxazoline to 3-[(tertbutoxycarbonyl)amino]benzyl-p-toluenesulphonate) of 50:1 and in the case of macromer 1c a monomer/initiator ratio of 100:1 was chosen.

The macromers 1a, 1b and 1c were characterized via FT-IR-, $^1$H- and $^{13}$C-NMR examinations as well as by GPC measurements. The spacer length or the degree of polymerization follows from the ratio of the surface integrals of the $^1$H-NMR signals of the end-group to those of the spacer signals.

Macromer 1a Mn=2720 (g/mol)
 degree of polymerization n=25

Macromer 1b Mn=6120 (g/mol)
 degree of polymerization n=65

Macromer 1c Mn=11820 (g/mol)
degree of polymerization n=132

Example 2

Preparation of Macromers with Polyoxazoline Spacer Beginning with Antimicrobial Group

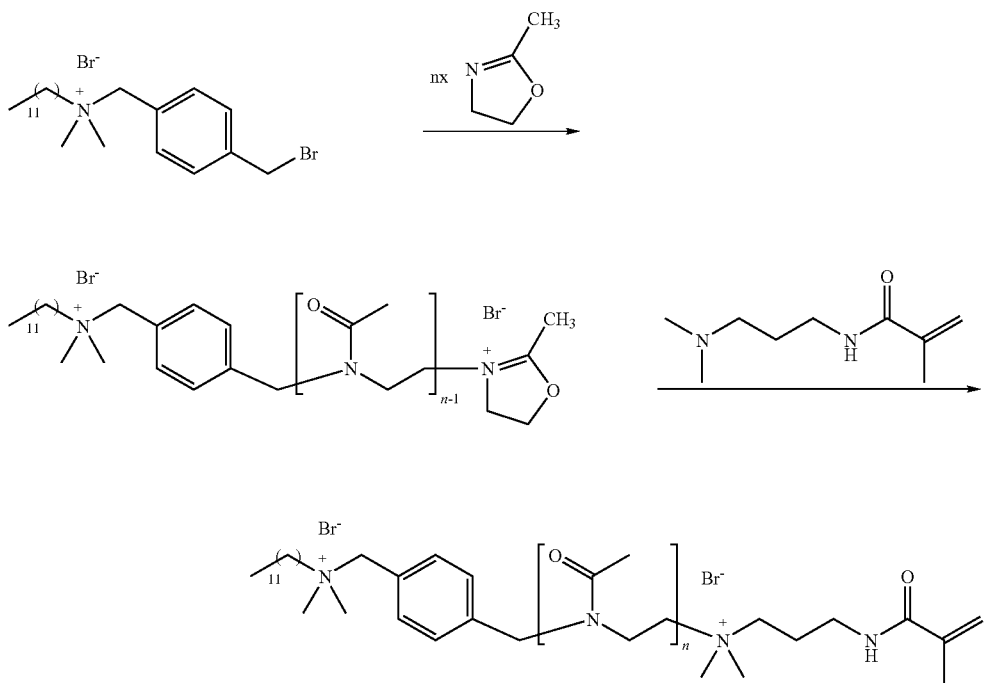

0.3 g (1/100 equiv.) of the initiator (4-bromomethyl-benzyl)-N,N-dimethyldodecylammonium bromide was added at 0° C. to a solution of 2-methyl-1,3-oxazoline (5.0 g) in 25 ml CHCl$_3$. After 30 min, the mixture was heated to 70° C., and the batch was stirred for three days. 3.1 g of the termination reagent N,N-dimethylaminopropylmethacrylamide was then added and the whole stirred for a further 24 h at 70° C. After precipitation three times from diethyl ether and dialysis in water at RT, 4.7 g (87% of the theoretical value) of the light-yellow, powdery macromer 2a was obtained.

Macromers 2b and 2c were prepared in the same way as macromer 2a, the difference being that for the preparation of macromer 1b a monomer/initiator ratio (2-methyl-1,3-oxazoline to (4-bromomethyl-benzyl)-N,N-dimethyldodecylammonium bromide) of 50:1 and in the case of macromer 2c a monomer/initiator ratio of 100:1 was chosen.

The macromers 2a, 2b and 2c were characterized via FT-IR-, $^1$H- and $^{13}$C-NMR examinations as well as by GPC measurements. The spacer length or the degree of polymerization follows from the ratio of the surface integrals of the $^1$H-NMR signals of the end-group to those of the spacer signals.

Macromer 2a Mn=2350 (g/mol)
degree of polymerization n=20

Macromer 2b Mn=5170 (g/mol)
degree of polymerization n=57

Macromer 2c Mn=10600 (g/mol)
degree of polymerization n=117

Example 3

Determination of the MIC Value of Macromers 1a-1c and 2a-2c

The minimal inhibitory concentration (MIC value) was determined analogously to the method described in the literature (A. H. Hogt, J. Dankert, J. Feijen, J. Biomed. Mater. Res. 1986, 20, 533).

50 ml of a sterile standard culture medium (Merck) was seeded with 100 µl of a suspension of *Staphylococcus aureus* cells (approx. 10$^{11}$ cells per ml) in PBS (phosphate buffer saline), pH 7.0, incubated for 6 h at 37° C. accompanied by shaking and then diluted with culture medium to 10$^5$ cells per ml (determination of concentration by absorbance measurement at 540 nm; E=1 corresponds to 10$^9$ cells per ml). 100 µl of the macromer to be tested was then added dissolved in culture medium to 1 ml of the bacterial suspension. The mixture was incubated again at 37° C. for 4-6 h accompanied by shaking, and the absorbance at 540 nm was measured at clearly visible clouding of the control sample (bacterial suspension without macromer). The MIC value is the minimum macromer concentration at which the absorbance value of the sample is more than 100 times less than the value of the control sample, i.e., at which growth is inhibited in 99% of the bacteria. The results are shown in Table 1.

TABLE 1

MIC values of the macromers 1a-1c and 2a-2c

| Macromer | MIC [mg/ml] | MIC [µmol/l] |
|---|---|---|
| 1a | 0.2 | 85 |
| 1b | 0.4 | 69 |
| 1c | 1.0 | 84 |
| 2a | 0.02 | 8 |
| 2b | 0.04 | 8 |
| 2c | 0.08 | 7 |

Example 4

Preparation of Dental Adhesives Based on Macromers 1a-c and 2a-c

To examine the antimicrobial effect of the macromers of Formula (I) in dental materials, adhesives with the following compositions were prepared:

Adhesive A:

(i) 14 wt.-% of the cross-linker glycerol dimethacrylate (GDMA);

(ii) 75 wt.-% of the hydrophilic monomer 2-hydroxyethyl methacrylate;

(iii) 10 wt.-% of the antimicrobial macromer 1a, 1b or 1c;

(iv) 0.5 wt.-% of the photoinitiator Genocure EPD and 0.5 wt.-% of the initiator camphorquinone.

Adhesive B:

(i) 15 wt.-% of the cross-linker glycerol dimethacrylate (GDMA);

(ii) 81 wt.-% of the hydrophilic monomer 2-hydroxyethyl methacrylate;

(iii) 3 wt.-% of the antimicrobial macromer 2a, 2b or 2c;

(iv) 0.5 wt.-% of the photoinitiator Genocure EPD and 0.5 wt.-% of the initiator camphorquinone.

Adhesive C:

(i) 45 wt.-% of the cross-linker glycerol dimethacrylate (GDMA);

(ii) 24 wt.-% of the hydrophilic monomer 2-hydroxyethyl methacrylate;

(iii) 30 wt.-% of the antimicrobial macromonomer 2a, 2b or 2c, (iv) 0.5 wt.-% of the photoinitiator Genocure EPD and 0.5 wt.-% of the initiator camphorquinone.

The above adhesives were applied to a slide and photopolymerized using a UV lamp. The resulting clear polymer film was then washed for two days with water.

Antimicrobial Examination

In a Petri dish, a modified slide was covered with 30 ml of a *Staphylococcus aureus* suspension in PBS ($\rightarrow 10^7$ bacteria cells/ml) and then incubated accompanied by light shaking (50 rpm) for 1 h at 37° C. The bacterial suspension was then drawn off and the slide was washed with pure PBS (15+15 ml). The slide was then dried, transferred to a new Petri dish, covered with 30 ml 1.5% nutrient agar and then incubated at 37° C. A blind sample was then analogously tested in each case using a slide which was coated with adhesive without biocidal macromer. After 12 h clear bacterial growth was evident on the blind sample whereas the samples with added antibacterial macromer remained free of any bacterial attack in all cases.

Example 5

Determination of the Adhesive Properties and Storage Stability of Dental Adhesives Based on Macromers 2a-c To examine the adhesive properties on tooth enamel and dentine and the storage stability of dental materials based on macromers of Formula (I), an adhesive of the following composition was prepared:

Adhesive D:

(i) 10 wt.-% of the macromonomer 2a, 2b or 2c;

(ii) 10 wt.-% of the acidic monomer 2-[4-(dihydroxyphosphoryl)-2-oxa-butyl]-acrylic acid ethyl ester (DHPAE);

(iii) 10 wt.-% hydroxyethyl methacrylate (HEMA);

(iv) 30 wt. % bisphenol A-diglycidyl ether dimethacrylate (bis-GMA);

(v) 20 wt. % glycerol dimethacrylate (GDMA);

(vi) 19 wt.-% ethanol;

(vii) 0.5 wt.-% of the photoinitiator Genocure and 0.5 wt.-% of the initiator camphorquinone.

This is a composition which is suitable as a dental adhesive for enamel and dentine.

Adhesivity Tests (Shearing Adhesive Strength)

Bovine teeth cast in resin were used for the dentine/enamel-adhesion measurements (Bühler Castolite resin). Firstly, the cast bovine tooth was ground down approximally with P500 sandpaper to the dentine or enamel. After brief fine-grinding with P1000 sandpaper and thorough washing off under running water, the tooth was prepared for the testpiece production.

The procedure for this was as follows: phosphoric acid etching gel (Emailpräparator GS, Ivoclar Vivadent AG) was applied to the dentine or enamel surface and washed off with water after an action time of 30 s. The thus-conditioned surface was lightly blotted dry with a paper tissue and the adhesive formulation to be tested then applied. After an action time of 10 seconds, the adhesive was polymerized with a polymerization lamp (Astralis® 7) for 20 seconds. The thus-prepared tooth was clamped in an adhesion mould and the composite applied by means of a round Delrin mould 4 mm in diameter (max. 3 mm in total) in two layers, each of which was illuminated for 40 s with Astralis® 7 (>500 mW/cm$^2$). The thus-prepared testpiece was demolded and immediately placed in water. After storage of all the testpieces (number of testpieces n=6) at 37° C. for 24 h, the adhesive strength was ascertained by means of a Universal Test Machine (Zwick Z010) and a testpiece device (guillotine) at a speed of 0.8 mm/min. (ISO/TS 11405; Dental materials—testing of adhesion to tooth structure. 2003).

The adhesion values of the adhesives based on macromers 2a, 2b and 2c compared with an analogous adhesive formulation without addition of macromonomer (comparative sample) are shown in Table 2.

TABLE 2

Adhesion values of adhesives based on macromers 2a-c

| Macromer | Mn (g/mol) | Enamel adhesion (MPa) | Dentine adhesion (MPa) |
|---|---|---|---|
| 2a | 2350 | 22.5 ± 4.2 | 15.9 ± 2.0 |
| 2b | 5170 | 20.6 ± 4.0 | 16.7 ± 1.6 |
| 2c | 10600 | 18.6 ± 4.3 | 18.9 ± 6.8 |
| Comparative sample | — | 24.4 ± 4.8 | 19.6 ± 2.7 |

As Table 2 shows, the addition of a macromer of Formula 2a, 2b or 2c does not have a negative effect on the dentine/enamel-adhesion properties of a dental adhesive.

Example 6

Preparation of a Dental Fixing Cement Based on the Macromer 2c

To examine the mechanical properties of dental materials based on macromers of Formula (I), a composite-based dental fixing cement with the following composition was prepared:

(i) 1 wt.-% of the antibacterial macromonomer 2c (ii) 24 wt.-% of a mixture of polyfunctional monomers (bis-GMA, UDMA and ethoxylated bisphenol-A-dimethacrylate)

(iii) 6 wt.-% of a mixture of monofunctional methacrylates (2-dimethylaminoethyl- and 2-hydroxyethylmethacrylate)

(iv) 0.6 wt. % initiators (benzoyl peroxide and 3,5-di-tert-butyl-N,N,-diethylaniline)

(v) 0.1 wt. % stabilizers (2,2,6,6-tetramethylpiperidine-1-oxyl and D-T-butyl-P-cresol)

(vi) 68.3 wt. % inorganic fillers (glass powder, ytterbium trifluoride, Si/Zr mixed oxide, titanium dioxide, pyrogenic silica)

The compressive strength of this fixing cement and of a comparative sample were measured as described in EN ISO 9917-1:2003 in Appendix D. The results are shown in Table 3.

TABLE 3

Compressive strength of a cement based on the macromer 2c

| Cement | Mn (g/mol) | Compressive strength |
|---|---|---|
| With macromer 2c | 10.600 | 275 ± 30 MPa |
| Comparative sample[1)] | — | 295 ± 25 MPa |

[1)]Fixing cement without antimicrobial macromer, the macromer 2c was replaced by a 1:1 mixture of ethoxylated bisphenol-A-dimethacrylate and 2-hydroxyethylmethacrylate As Table 3 shows, the addition of the macromer 2c does not have a significant effect on compressive strength and thus does not adversely affect the suitability of the material as a fixing cement.

Example 7

Preparation of a Dental Adhesive Based on the Antimicrobial Monomer 12-methacryloyloxydodecylpyridiunium Bromide (MDPB)

Comparative Example

For comparison purposes, a dental adhesive based on the antimicrobial monomer 12-methacryloyloxydodecylpyridinium bromide (MDPB, synthesized according to EP 0 602 254 and characterized by $^1$H-NMR spectroscopy) with the following composition was prepared:

(i) 20 wt.-% of the cross-linker glycerol dimethacrylate (GDMA);

(ii) 74 wt.-% of the hydrophilic monomer 2-hydroxyethylmethacrylate;

(iii) 5 wt.-% of the monomer MDPB;

(iv) 0.5 wt.-% of the photoinitiator Genocure EPD and 0.5 wt.-% of the initiator camphorquinone.

The comparative material displays a similar composition to the adhesive described in Example 4. The mixture was applied to a slide and photopolymerized with the help of a UV lamp. The resulting clear polymer film was then washed for two days with water. The antimicrobial testing then took place as described in Example 4. A slide which had been coated with adhesive without the biocidal monomer MDPH served as comparison. The comparative sample displayed clear bacterial growth, while the sample with MDPH displayed no bacterial attack.

It was striking that, in the case of the films with MDPB addition, not only was no bacterial decay attack on the film itself, but a clearly recognizable inhibitory halo had formed around the slide. A halo is a clear indication that a large part of the antimicrobial active ingredient has not been immobilized and is diffusing out of the film into the culture medium. Such a release of antimicrobial, potentially toxic monomers is undesired with dental materials.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A dental material comprising at least one compound of Formula (I),

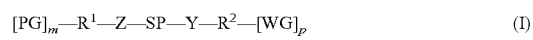

in which m=1, 2 or 3;

p=1, 2 or 3;

$R^1$=is absent, a linear or branched $C_1$ to $C_{20}$ alkylene radical which can be interrupted one or more times by O, S, NH, $SiR'_2$, CONH, CONR', COO and/or OCONH, aromatic $C_6$ to $C_{14}$ radical or a combination thereof;

$R^2$=is absent, a linear or branched $C_1$ to $C_{20}$ alkylene radical which can be interrupted one or more times by O, S, NH, SiR'$_2$, CONH, CONR', COO and/or OCONH, aromatic C$_6$ to C$_{14}$ radical or a combination thereof;

PG=a radically polymerizable group;

SP=a polymeric spacer which is selected from polyglycerol, polyalkyloxazoline, polyethyleneimine, polyacrylic acid, polymethacrylic acid, polyvinyl alcohol, polyvinyl acetate, poly-(2-hydroxyethyl)acrylate, poly-(2-hydroxyethyl)methacrylate groups, hydrophilic polypeptide groups and copolymers of the corresponding monomers;

WG=an antimicrobially active group;

Z=is absent, O, S, an ester, amide or urethane group;

Y=is absent, O, S, an ester, amide or urethane group;

R'=independently in each case a linear or branched C$_1$ to C$_{20}$ alkylene radical, phenyl or benzyl radical;

and which has a molecular weight (Mn) of at least 1,000.

2. The dental material according to claim 1, wherein the polymerizable group PG is a vinyl, allyl, vinyl ether, styryl, vinylcyclopropyl, (meth)acryloyl, (meth)acrylamide group and/or a group of Formula (II),

Formula (II)

in which R$^{13}$ is methyl or phenyl.

3. The dental material according to claim 1, wherein the antimicrobially active group WG is a primary, secondary, or tertiary amino group, a cationic primary, secondary, tertiary or quaternary ammonium, phosphonium or sulphonium group, a biguanidine group, an antimicrobial peptide, a phenol or polyphenol radical and/or an antibiotic.

4. The dental material according to claim 1, wherein in which the spacer SP is an —[R$^3$]$_q$— group in which R$^3$ is —[CH$_2$—CH$_2$—O]—, —[CH(CH$_3$)—CH$_2$—O]—, —[CH(OH)CH$_2$]—, —[CH(COOH)CH$_2$]—, —[CH(COOCH$_3$)CH$_2$]—, —[C(CH$_3$)(COOH)CH$_2$]—, —[C(CH$_3$)(COOCH$_3$)CH$_2$]—, —[CH(COOCH$_2$CH$_2$OH)CH$_2$]—, —[C(CH$_3$)(COOCH$_2$CH$_2$OH)CH$_2$]—, —[CH(OCOCH$_3$)CH$_2$]—, —[CH$_2$—CH(OH)—CH$_2$—O]—, —[R$^4$—N(—CO—R$^6$)—R$^5$]— or a combination thereof, wherein R$^4$=is absent, a linear or branched C$_1$ to C$_{20}$ alkylene radical which can be interrupted by one or more O atoms, aromatic C$_6$ to C$_{14}$ radical, —(CH$_2$)$_{1-4}$— or is absent;

R$^5$=is absent, a linear or branched C$_1$ to C$_{20}$ alkylene radical which can be interrupted by one or more O atoms, aromatic C$_6$ to C$_{14}$ radical, —(CH$_2$)$_{1-4}$— or is absent;

R$^6$=a linear or branched C$_1$ to C$_{20}$ alkyl radical, aromatic C$_6$ to C$_{14}$ radical, C$_1$-C$_3$ alkyl;

q=10 to 15,000.

5. The dental material according to claim 1, wherein at least one of the variables has one of the following meanings:

m=1 or 2;

p=1 or 2;

R$^1$=is absent, a linear or branched C$_1$ to C$_4$ alkylene radical which can be interrupted once by COO; phenylene, benzylene, —CH$_2$—Ph—CH$_2$—;

R$^2$=is absent, a linear or branched C$_1$ to C$_4$ alkylene radical which can be interrupted once by COO, phenylene, benzylene, —CH$_2$—Ph—CH$_2$—;

PG=CH$_2$=CR$^{10}$—CO—X— with R$^{10}$=H or CH$_3$ and X=O, NH, NR$^{12}$, wherein R$^{12}$ is a linear C$_1$ to C$_5$ alkyl radical, CH$_2$=CH— or vinylcyclopropyl;

Z=is absent, O, S, COO;

Y=is absent, O, S, COO;

A$^-$=Cl$^-$, Br$^-$, I$^-$, mesylate (Mes), tosylate (Tos) or triflate (Trf);

WG=—N$^+$R$^7$R$^8$R$^9$A$^-$, with

R$^7$=H, a linear or branched C$_1$ to C$_{20}$ alkyl radical, or R$^7$ forms together with R$^8$ and the nitrogen atom to which it is bonded an aromatic or heteroaromatic ring system or an aromatic or non-aromatic ring

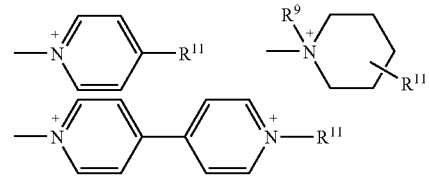

R$^8$=H, a linear or branched C$_1$ to C$_{20}$ alkyl radical or R$^8$ forms together with R$^7$ and the nitrogen atom to which it is bonded an aromatic or heteroaromatic ring system or an aromatic or non-aromatic ring; and R$^9$=is absent, H, a linear or branched C$_1$ to C$_{31}$ alkyl radical or —P$^+$R$^{7'}$R$^{8'}$R$^{9'}$A—, with R$^{7'}$=H, a linear or branched C$_1$ to C$_{20}$ alkyl radical;

R$^{8'}$=H, a linear or branched C$_1$ to C$_{20}$ alkyl radical; and

R$^{9'}$=is absent, H, a linear or branched C$_1$ to C$_{20}$ alkyl radical;

or

r=5 to 30.

6. The dental material according to claim 5, wherein the compound of Formula (I) is a compound of Formula (I"):

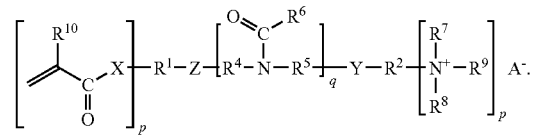

Formula (I")

7. The dental material according to claim 1, wherein the compound of Formula (I) has a molecular weight (Mn) of at least 2,500.

8. The dental material according to claim 1, wherein the compound of Formula (I) has a molecular weight (Mn) of at least 5,000.

9. The dental material according to claim 1, further comprising at least one further radically polymerizable monomer.

10. The dental material according to claim 9, wherein the at least one further radically polymerizable monomer comprises 2 to 3 radically polymerizable groups.

11. The dental material according to claim 9, wherein the at least one further radically polymerizable monomer comprises at least one acidic radically polymerizable monomer.

12. The dental material according to claim 1, further comprising at least one initiator for the radical polymerization.

13. The dental material according to claim 1, further comprising at least one filler.

14. The dental material according to claim 1, wherein the material comprises:
(a) 0.05 to 50.0 wt.-% radically polymerizable compound of Formula (I);
(b) 5 to 95 wt.-% further radically polymerizable monomer; and
(c) 0.01-5.0 wt.-% initiator for the radical polymerization.

15. The dental material according to claim 14, further comprising:
(d) 0 to 60 wt.-% acidic radically polymerizable monomer.

16. The dental material according to claim 14, further comprising:
(d) 0 to 85 wt.-% filler.

17. The dental material according to claim 15, further comprising:
(e) 0 to 85 wt.-% filler.

18. The dental material according to claim 14, further comprising:
(d) 0 to 80 wt.-% solvent.

19. The dental material according to claim 15, further comprising:
(e) 0 to 80 wt.-% solvent.

20. The dental material according to claim 17, further comprising:
(f) 0 to 80 wt.-% solvent.

21. An adhesive, cement, coating material or filling material comprising the dental material of claim 1.

22. A process for preparing a molding comprising shaping the dental material of claim 1 to form a molding and curing the molding.

23. The dental material according to claim 5, wherein the aromatic or heteroaromatic ring system or aromatic or non-aromatic ring of $R^7$ is one of the following:

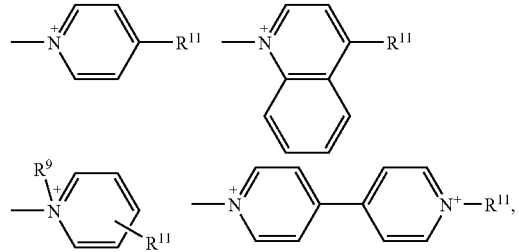

wherein $R^{11}$ is a linear or branched $C_1$ to $C_{20}$ alkyl radical.

24. The dental material according to claim 1, wherein $R^1$, $R^2$ and/or $R'_m$ are substituted by $C_1$-$C_6$ alkyl, $C_1$-$C_6$ alkoxyl, aryl, benzyl, F, Cl, Br, I, HO, HOOC, $C_1$-$C_6$ alkyl-OOC—, $H_2$NOC, HR"OC, or R"$_2$OC, wherein R" is a $C_1$-$C_{20}$ alkylene, phenyl or benzyl.

25. The dental material according to claim 5, wherein $R^9$ is $(CH_2)_r$— and r=5 to 30, or wherein $R^{9'}$ is $(CH_2)_r$— and r=5 to 30.

* * * * *